(12) United States Patent
Mokkila

(10) Patent No.: US 8,772,517 B2
(45) Date of Patent: Jul. 8, 2014

(54) METHOD OF PRODUCING A PRODUCT BASED ON VEGETABLE OIL

(75) Inventor: Kosti Mokkila, Espoo (FI)

(73) Assignee: Neste Oil Oyj, Espoo (FI)

( * ) Notice: Subject to any disclaimer, the term of this patent is extended or adjusted under 35 U.S.C. 154(b) by 610 days.

(21) Appl. No.: 12/937,249

(22) PCT Filed: Apr. 14, 2009

(86) PCT No.: PCT/FI2009/050277
§ 371 (c)(1),
(2), (4) Date: Dec. 9, 2010

(87) PCT Pub. No.: WO2009/125072
PCT Pub. Date: Oct. 15, 2009

(65) Prior Publication Data
US 2011/0092724 A1    Apr. 21, 2011

(30) Foreign Application Priority Data
Apr. 10, 2008 (FI) .................................... 20085300

(51) Int. Cl.
*C11B 3/00* (2006.01)
*C07C 69/76* (2006.01)
*C07C 39/00* (2006.01)
*C07C 15/12* (2006.01)

(52) U.S. Cl.
USPC ............... 554/124; 554/220; 560/8; 568/744; 585/25

(58) Field of Classification Search
USPC .......... 554/124, 220; 560/8; 568/744; 585/25
See application file for complete search history.

(56) References Cited

U.S. PATENT DOCUMENTS

| 4,495,094 | A | 1/1985 | Cleary |
| 2002/0198159 | A1* | 12/2002 | Courbiere et al. .............. 514/25 |
| 2005/0033027 | A1* | 2/2005 | Rohr et al. .................... 530/359 |
| 2009/0215881 | A1 | 8/2009 | Delaire et al. |

FOREIGN PATENT DOCUMENTS

| EP | 0141271 A2 | 5/1985 |
| EP | 0952208 A2 | 10/1999 |
| EP | 1173463 A1 | 1/2002 |

(Continued)

OTHER PUBLICATIONS

Shostakovskii, S.F. et al. Hydroxystilbenes of *Pinus sibirica* and *Pinus silvestris*. Khimiya Prirodnykh Soedinenii, 1969, vol. 5, No, 1, pp. 48-49, English abstract.*

(Continued)

*Primary Examiner* — Deborah D Carr
(74) *Attorney, Agent, or Firm* — Birch, Stewart, Kolasch & Birch, LLP

(57) ABSTRACT

A composition, which is suitable for the production of stilbene compounds, can be separated from tall oil. It contains esters of pinosylvin or pinosylvin derivatives and it is concentrated in relation to these. Preferably, the composition contains esters of pinosylvin monomethyl ethers, the acid part of which is formed of an inorganic acid or an organic acid, in particular an organic acid, which is present in the crude tall oil or which is generated from this oil during the process of refining it. Typically, such acids are fatty and resin acids and lower alkane acids. With the invention, it is possible to generate, at an industrial scale, product fractions, and the pinosylvin compounds which are separated from the fractions can be used as such or they can be further modified by means of different chemical methods.

29 Claims, 1 Drawing Sheet

(56) References Cited

FOREIGN PATENT DOCUMENTS

| | | | |
|---|---|---|---|
| FI | 66195 | A | 10/1981 |
| FI | 75595 | A | 5/1985 |
| GB | 2072656 | A | 10/1981 |
| JP | 6029216 | A | 2/1994 |
| JP | 8175960 | A | 7/1996 |
| WO | WO-0142231 | A2 | 6/2001 |
| WO | WO-2004080942 | A1 | 9/2004 |
| WO | WO-2006134282 | A1 | 12/2006 |
| WO | WO-2009125072 | A1 | 10/2009 |

OTHER PUBLICATIONS

Park, E-J. et al. Synthesis and inhibitory effects of pinosylvin derivatives on prostaglandin E2 production in lipopolysaccharide-induced mouse macrophage cells. Bioorganic & Medicinal Chemistry Letters, 2004, vol. 14, No. 23, pp. 5895-5898.*

Holmbom, Bjarne and Eero Avela. "Studies on Tall Oil From Pine and Birch." Institute of Wood Chemistry and Cellulose Technology. Sep. 1971; vol. 31 No. 16: pp. 1-18.

Park, Eun-Jung et al.. "Synthesis and inhibitory effects of pinosylvin derivatives on prostaglandin $E_2$ production in lipopolysaccharide-induced mouse macrophage cells" Bioorganic and Medicinal Chemistry Letters. Sep. 28, 2004; vol. 14: pp. 5895-5898.

Shostakovskii, S.F. et al. "Hydroxystilbenes of *Pinus sibrica* and *Pinus silvestris*" Irkutsk Institute of Organic Chemistry. Jul. 26, 1968; vol. 5 No. 1: pp. 41.

Wang, Shi-Fa et al. "Composition of neutral fractions in Chonese raw tall oil" Journal of Wood Science. Sep. 27, 2001; vol. 47: pp. 400-405.

\* cited by examiner

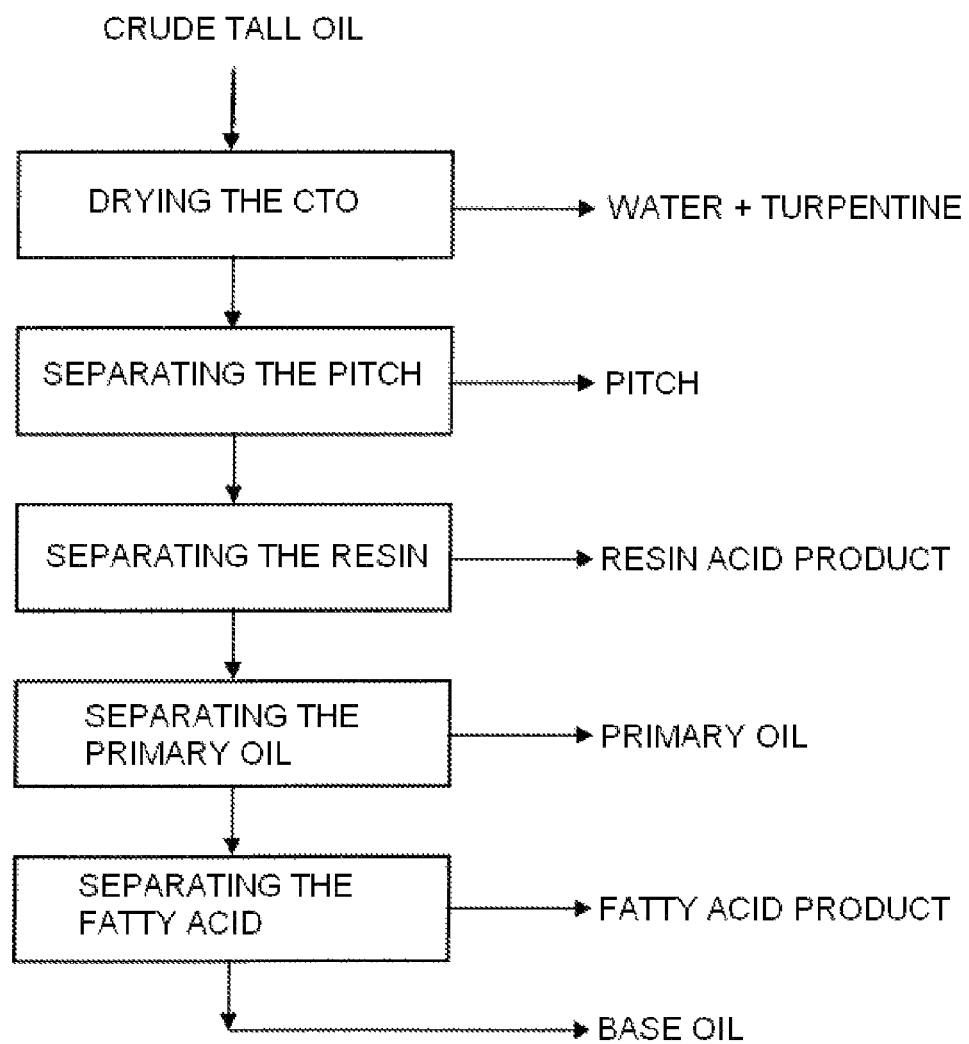

METHOD OF PRODUCING A PRODUCT BASED ON VEGETABLE OIL

This Application is the National Phase Under 35 U.S.C. §371 of PCT International Application No. PCT/FI2009/050277 which has an International filing date of Apr. 14, 2009, which claims priority to Finnish Application No. 20085300 filed on Apr. 10, 2008, The entire contents of all applications listed above are hereby incorporated by reference.

The present invention relates to a composition according to the preamble of claim 1.

The present invention also relates to a method of producing a composition which is suitable for manufacturing stilbene compounds, according to the preamble of claim 13.

Furthermore, the present invention relates to a method of manufacturing stilbene and its derivatives from compositions which comprise pinosylvin or its derivatives.

Tall oil naturally comprises stilbene compounds. Examples of stilbene compounds are, among others, trans- and cis-stilbene, and resveratrol, piceatannol and pinosylvin. Typically, these compounds comprise two benzene rings and between them an ethenylene chain, in which case there are hydroxy substituents in the last three mentioned compounds, either in one benzene ring or in both of them.

These compounds are formed during normal tree growth. When pulp is manufactured from wood by using the sulphate method, the stilbene compounds are at least partly transferred into a by-product, namely a crude tall oil flow of the pulp process. In the literature, stilbene compound percentages of tall oil have been analysed, but on the basis of the results the amounts have, however, been estimated to be so small that commercial separation and recovery of the stilbene compounds from tall oil have previously not even been considered.

The purpose of the present invention is to generate a method of recovering stilbene compounds, in particular pinosylvin and its derivatives, from crude tall oil (hereinafter CTO) and from products generated by the evaporation and distillation of that crude tall oil. Another purpose of the present invention is to generate compositions which comprise esters of pinosylvin and of pinosylvin monomethyl ether, and a method of producing such compositions.

The present invention is based on the discovery that stilbene compounds, in particular pinosylvin compounds, migrate into the different product fractions generated by the distillery of tall oil, according to their molecular weight and how distillable they are. Pinosylvin and its monomethyl ether react under suitable conditions, in association with the process of distilling CTO, to form, among others, esters of fatty acids and resin acids, in which case their molecular size typically increases. In that case, they can be easily separated from the actual product flows of the distillation process, which flows contain, among others, fatty acids and/or resin acids.

Unexpectedly, it has also been found that the compounds concentrate particularly in such distillation fractions which, not being useful for further processing, have until now been removed and burnt or used for otherwise secondary applications. In association with the present invention it has been found that the fractions in question comprise—in contrast to what has been observed earlier—such large amounts of these stilbene compounds that, after concentration, they form a most interesting initial material for the production of stilbene compounds.

More specifically, the composition according to the present invention is mainly characterized by what is stated in the characterizing part of claim 1.

The method according to the present invention is, in turn, characterized by what is stated in the characterizing part of claim 13.

The compounds according to the present invention are, in turn, characterized by a fatty acid ester of pinosylvin or of its monomethyl ether and a resin acid ester of pinosylvin or if its monomethyl ether.

Considerable advantages are obtained by means of the present invention. Thus, by means of the process presented here, it is possible to separate from tall oil, at an industrial scale, totally new, valuable compounds and product fractions which comprise these compounds, which to date have not been widely available on the market. The pinosylvin compounds, which are separated in this way, can be used as such or further modified by means of different chemical methods.

Recent research suggests that stilbene compounds offer great potential for development into health affecting food supplements or even pharmaceuticals. According to the present invention, a composition is generated, which is a suitable raw material for producing stilbene compounds, and which contains for instance fatty acid esters of pinosylvin monomethyl ether, and resin acid esters of pinosylvin monomethyl ether. From these compounds it is possible to manufacture, in addition to the above-mentioned pinosylvin monomethyl ether, also numerous other stilbene derivatives, such as pinosylvin, piceatannol, resveratrol, rhapontigenin and pterostilbene.

In the present invention, the stilbene compounds mean in particular these compounds mentioned just above along with their derivatives.

In the following, the present invention will be examined more closely with the aid of a detailed description and the accompanying drawing. The Figure shows a typical block diagram of a tall oil distillery.

As described above, the present invention is based on the discovery that the fractions generated by the distillation or evaporation of CTO, including the bottoms products of the distillation columns and of the evaporation units, comprise unexpectedly large quantities of stilbene compounds and esters of these, and consequently these fractions are suitable as initial materials for the recovering of such compounds.

In the present invention, "tall oil" means a material which is generated as a by-product in the manufacturing process of pulp, and which contains extractives of the wood which is used in the pulp cooking.

The main components of the tall oil are fatty acids, resin acids and neutral compounds. The fatty acids are typically straight-chained saturated carboxylic acids, which are formed of 16-24 carbons, or carboxylic acids, which contain 1-3 double bonds. Industry and commerce are mainly interested in the $C_{18}$ fatty acids, which form the bulk of the fatty acids of the tall oil. Similarly, the resin acids of the tall oil are carboxylic acids but the bulk of their carbon structure is formed of three rings. Several different types of resin acids are present in tall oil and they differ from each other mainly regarding their different side groups and the number and location of their double bonds.

The pinosylvin compounds may occur in the tall oil as pure compounds, the most typical examples of which are pinosylvin (PS), pinosylvin monomethyl ether (PSME) and pinosylvin dimethyl ether (PSDME).

FIG. 1 shows a typical block diagram of a tall oil distillery.

As the figure shows, the CTO is processed in several stages before it is possible to separate and recover from the tall oil the resin acids and fatty acids contained in it.

The tall oil is distilled in conditions of underpressure because the vapour pressures of the materials to be processed are very low. Furthermore, at elevated temperatures, the materials tend to decompose into worthless compounds and, hence, it is aimed to keep the process conditions as moderate as possible. In Europe, a "dry process" is typically applied in the process of distilling tall oil, the operating pressure of which process is at the level of 3-30 mbar(a). In other parts of the world, typically a "wet process", i.e. steam distillation having a process pressure at the level of 250 mbar(a), is used.

Typically, the required underpressure is generated by using several steam generators in series, or by ejectors and a liquid ring pump in series. The underpressure, which is needed in the first stage of the distillation, i.e. the drying of the tall oil, and which underpressure is slightly lower than in the distillation process, is usually generated with only a liquid ring pump.

The CTO coming from the pulp mill contains approximately 2% water. In the dry distillation process, this percentage of water is detrimental to the operation of the vacuum devices. Consequently, the CTO is dried in the first stage, after which the water and the primary oil in the overhead product are separated from each other. The drying can be carried out for instance by leading the CTO, before the separation of pitch, typically into a thin film evaporator in which the operating pressure is approximately 40 mbar(a) and the temperature typically 200-240° C.

In the drying stage, the free water and the turpentine and other lighter components are removed from the CTO in the form of evaporation yield. The yield is condensed before it reaches the vacuum unit and in most cases it is combined with the ejector oil flow coming from the ejectors. After the drying, the CTO is generally led directly to the pitch removal, which is typically formed of two thin film evaporators in series or a separate pitch column The purpose of this stage is to separate as carefully as possible all the easily evaporating components of the CTO from those components that are poorly evaporating. The easily evaporating components are removed from the evaporators as a gaseous product flow and directed, either directly as a gas or via evaporation, as a liquid, into the resin column.

In addition to the gas flow exiting from the vacuum units, a mixture of water and the lightest organic components is also typically generated, the organic and aqueous phase of which are separated from each other typically by means of gravitational decanting. The organic phase, which is generally known as the ejector oil, typically contains turpentine and the very lightest acids and neutral compounds which form part of the CTO.

Ejector oil is generally generated in the range of 2-4% of the CTO. The water which is removed during the decanting, contains, besides the water or the steam condensate which the vacuum units utilize as their means of operation, also the water which is contained in the wet CTO, and which is generally below 2% of the amount of the CTO. The ejector oil is generally used as a fuel in the hot oil boiler of the distillery.

When Nordic CTO is distilled, the yield of pitch is approximately 30% of the dry CTO. The greater part of this pitch is used as biofuel. Pitch contains approximately 10-15% of sitosterol, either as a free compound or as esters. As a result, there are companies in the world which separate the sitosterol from the pitch in order to sell the sitosterol for further use in the production of food additives for health affecting foodstuffs.

The fraction of the distillation of the separated pitch is brought into the resin column, where the resin acids are separated from it in the form of the bottoms product, and the lighter fractions are recovered as overhead product. After that, from the surplus, generally the primary oil is separated in the first column and the fatty acid in the second column The fatty acid is typically recovered as a fraction of the distillation in the second column, which generates base oil as its bottoms product. Besides the resin acids and the heavy fatty acids from the preceding distillation stages, also the poorly evaporating components which are generated in association with the distillation, are concentrated on the bottom of the fatty acid column. Generally, this flow is combined directly with the pitch and, consequently, it is finally used as a bio fuel for energy production. The bottoms product in the fatty acid column is generated typically 4-6% of the amount of the CTO. The aim is to concentrate the $C_{18}$ acids, which form part of the tall oil, in the fatty acid fraction described above. When Nordic tall oil is distilled, the fatty acid yield is typically 35-40% of the dry tall oil introduced. The fatty acids are typically used in the production of alkyds, i.e. binding agents for paints, by preparing esters of a fatty acid and some polyalcohol.

The resin acids are concentrated in resin acid products, the yield of which in the Nordic countries is approximately 22-25% of the dry CTO. The resin acids are used for instance in the production of different esters and glues.

In distilleries which have a low separative efficiency, also a product fraction, which is known as distilled tall oil, must be drawn-off from the process in order to generate fatty and resin acids which are pure enough. This fraction mainly contains fatty acids, and in addition 25-35% of resin acids and a small percentage of neutral compounds. The heaviest, and thus the least evaporating, components of the tall oil exit the distilling process as a product fraction which is known as the tall oil pitch. The short chain (typically $C_{16}$) fatty acids and the light neutral compounds, which form part of the CTO, are concentrated in the primary oil. Generally, the primary oil is drawn-off at the upper end of each distillation column, but in the most advanced distilleries, only from the primary oil column. In the Nordic countries, the primary oil is typically approximately 7% of the amount of the dry CTO. To date, no further refining applications for primary oil exist and, accordingly, this oil is mainly used as a fuel based on renewable natural resources.

In both of the main process alternatives, the temperature of the top of the columns are generally in the range of 160-180° C. and the bottom temperatures of the columns in the range of 240-275° C. The hottest stage of the tall oil process occurs during the separation of the pitch, the temperature of which is typically in the range of 300-320° C.

When a pitch column is used for separating pitch, the evaporating components, which go for further distillation, are separated from the upper part of the column, and the pitch forms the bottoms product of the column.

During the pitch separation, the bottoms product obtained is tall oil pitch. From the main distillation process, at least the bottoms product of the resin column, which product contains both large amounts of heavy components and also lots of recoverable resin acids, is often returned to the pitch separation. The conditions of the pitch stage are typically 10-30 mbar(a) and 300-320° C.

The gas and/or liquid flow coming from the pitch removal is directed into the resin column. From this column, typically four fractions are drawn-off: from the top of the column, in most cases a small primary oil flow is drawn off; and below it a crude fatty acid fraction is fed further into the primary oil column; from the lower part of the column, a gaseous resin acid fraction is taken for immediate condensation; and from the bottom boiler, the return flow to the pitch separation. In addition, in older distilleries, the distilled tall oil fraction (DTO) is drawn off from a point slightly above the draw-off of the resin acid fraction. Furthermore, some distilleries take also the resin acid product from the bottom part of the column or from its bottom boiler.

A resin distillation column is typically a column packed with filling plates, which are designed for vacuum distillation, the bottom boiler of which column is either a falling film evaporator or a forced circulation evaporator. The other columns—the primary oil column and the fatty acid column—of a typical tall oil distillery have the same basic structure as that of the resin column The crude fatty acid composition, coming from the resin acid column, is directed into the primary oil column Typically, two product flows come from the column: the primary oil from the top, and a flow which is known as the crude fatty acid 2, from the bottom.

Accurate separation of the primary oil is essential when the aim is to generate a fatty acid, the colour of which is as light as possible and which is colour stable. The bottoms product of the primary oil column is directed into the fatty acid column, from which typically three product fractions are drawn-off: from the top, again, primary oil, which is typically directed back into the primary oil column, from slightly below the top, the product fatty acid, and from the bottom boiler, a fraction which is called the bottoms oil.

Associated with the present invention, it has been found that when crude tall oil is processed in a tall oil distillery such as described above, the stilbene compounds are distributed into the different product fractions of the distillery. In the various processing and storage stages of the crude tall oil, it is possible that PS and PSME react further with the main components of the tall oil, namely the fatty acids and the resin acids, and form together with those above-mentioned fatty acids and resin acids, esters of pinosylvin or its monomethyl ether.

The behaviour of the esters of pinosylvin and its monomethyl ethers in the distillation process of tall oil differs significantly from the corresponding behaviour of acids or pinosylvin compounds. The esters are very poorly evaporating and they migrate into the bottoms products of the distillery, whereas the free stilbene compounds and the fatty acids and the resin acids migrate typically into other product fractions of the distillery.

In association with the present invention, it has also been found that the esterified stilbene compounds adversely affect the quality of the tall oil distillates by causing darkening of the colour of the distillates. Consequently, it is advantageous to separate them during the distillation process as carefully as possible from the main products of the distillery, i.e. from the fatty acids and the resin acids.

It is possible to recover the unreacted stilbene compounds from the distillate fractions of the tall oil distillery, whereas the stilbene compounds, which have been esterified with the fatty acids and/or resin acids, or stilbene compounds which have otherwise reacted and thus become less volatile, can be separated from the bottoms product fractions of the distillery.

If the stilbene derivatives are reacted into esters, in which the acid part is formed of an acid which has a very low molecular weight, it is possible to make the generated esters migrate into the distillation fractions, too.

Furthermore, it should be noted that it is also possible to separate the stilbene compounds from the compounds which have migrated into the vacuum system of the distillery, particularly if steam distillation is applied during the distillation of the tall oil.

According to the present invention, the composition generated, which is suitable for production of stilbene compounds, contains pinosylvin, a derivative of pinosylvin, an ester of pinosylvin or an ester of pinosylvin derivative, or mixtures of the listed compounds. Most suitably, the composition is concentrated, i.e. enriched in relation to these compounds. This "concentrating" includes, among others, the option in which other components are removed from the composition which contains stilbene derivatives, in which case the percentage of stilbene derivatives increases, and the option in which the stilbene derivatives are separated from the composition and recovered.

According to a preferred embodiment, the composition contains esters of pinosylvin monomethyl ether, the acid part of which esters is formed of an inorganic or organic acid, in particular an organic acid which is present in the crude tall oil or which is generated from crude tall oil during its refining processing. Typically, such acids are fatty acids and resin acids, and lower alkane acids.

Consequently, the acid part of the esters can for instance be derived from carboxylic acid, which contains a straight-chained hydrocarbon structure which includes 16-24 carbons and which is either completely saturated or which contains 1-3 double bonds. More preferably, the acid part of the ester of the pinosylvin monomethyl ether is derived from linoleic acid, linolenic acid or oleic acid.

It is also possible that the acid part of the ester of pinosylvin or pinosylvin monomethyl ether comes from a tricyclic, aliphatic or aromatic carboxylic acid. Examples of these acids are abietic acid, dehydroabietic acid, neoabietic acid, palustrene acid, pimaric acid and levopimaric acid.

The acid parts of the esters may come from one acid or from mixtures of two or more acids.

Generally, the pinosylvin compounds form approximately 0.1-20 weight-% of the fraction or bottoms product to be separated, but it is possible to concentrate this composition by separating the lighter components for instance by evaporation. After such a concentration stage, the percentage of the stilbene compounds is generally at least 3 weight-%, especially approximately 5-80 weight-%, especially approximately 5-50 weight-%, calculated of the total weight of the composition.

The share of the pinosylvin, the esters of pinosylvin, the pinosylvin monomethyl ether, the esters of pinosylvin monomethyl ether or the pinosylvin dimethyl ether, or a mixture of two or more compounds, of the composition, is approximately 1-95 weight-%, especially approximately 10-60 weight-%, more prefereably approximately 15-50 weight-%, calculated of the total weight of the composition.

Thus, according to an embodiment, the composition according to the present invention comprises tall oil pitch which is concentrated in order to increase the share of the esters in the stilbene compounds.

In the method according to the present invention, a fraction, which contains stilbene compounds, is recovered from a fraction of the distillation or the evaporation of the crude tall oil, and this fraction is enriched in relation to the stilbene compounds. This distillation or evaporation fraction is preferably an overhead product, a bottoms product or a side draw-off taken from a chosen intersection, or a flow which migrates into the vacuum system, from a distillation column or an evaporator.

In the distillation process of the tall oil, the esterified stilbene compounds migrate mainly into the pitch and particularly into the bottoms product of the fatty acid column.

Consequently, according to an embodiment, the fraction which contains esters of the stilbene compounds is recovered as the bottoms fraction of the fatty acid distillation column.

It is also possible to recover a mixture, which contains stilbene compounds or esters of these, as an overhead product of the distillation or evaporation stage of any distillation process of tall oil, but in particular as an overhead product of a distillation column of light fatty acids. The stilbene compounds which form part of the overhead product are esterified, if needed, but not necessarily, in order to facilitate concentration of them. Organic acid or mineral acid can be used as the esterifying acid. Examples of these are lower alkane acids, fatty acids and resin acids.

After the stilbene compounds are esterified, they are concentrated in relation to the overhead product but it is also possible to carry out the separation without any esterifying by using known separation methods of chemical technology.

The process flows generated by the distillation of tall oil, can also be combined in order to produce a suitable raw material. Accordingly, a composition which is particularly suitable for the production of stilbene compounds is achieved by combining the bottoms fraction of the fatty acid distillation column and the overhead product of the distillation of light fatty acids.

From the bottoms product of the fatty acid column, as well as from other flows generated by the distillation of tall oil, it is easy to concentrate the stilbene compounds by vaporizing the bottoms product at a low pressure. The vaporizing can take place for instance in a forced circulation evaporator, a falling film evaporator, a thin film evaporator or a short-path evaporator or some other device which is appropriate for underpressure evaporation. Alternative separation methods are, among others, repeated distillation, extraction, chromatographic separation, ion-exchange methods, adsorption, absorption, underpressure distillation and separation crystallization. In addition, different filtration methods, for instance membrane filtration, might be considered in the concentrating of the compounds.

The above-mentioned separation techniques can also be applied when the esters of the pinosylvin compounds are disintegrated prior to the separation process, either transforming them back to the initial products of the esters or to other compounds of these initial products. This reaction which disintegrates the esters can be carried out either in an aqueous or solvent environment by using, if needed, an auxiliary chemical which generates alkaline conditions, or another chemical which furthers the breaking-up of the esters.

Another possible separation technique is interesterification, in which the alcohol component of the ester, in this case the pinosylvin compound, is replaced by another alcohol.

It has been discovered that the pinosylvin compounds react in a normal distillation process of tall oil and form esters of fatty and resin acids. Because the esters are easier to separate from other tall oil components than are the free pinosylvin compounds, it is possible to facilitate the formation of esters by treating mixtures, which are to be distilled, in one or several process stages by adding into them an additive which catalyzes the esterification, for instance acid or compounds which release hydrogen ions (protons) when the compounds react with fatty or resin acids. It is known that the hydrogen ions (protons) which enter the mixture in association with the addition of the acid, or which are released through different reactions, catalyze the esterification reaction.

From the composition according to the present invention, the stilbene compounds are recovered as esters of different acids, particularly of mineral or alkane acids or fatty acids or resin acids, or as mixtures of these.

It is possible to separate the stilbene compounds, which are free from fractions, by using the same techniques as have been described above regarding the esters. The stilbene compounds can also be modified by means of other chemical technology methods to form such compounds which are easier to separate from the rest of the fraction than is the original compound. Accordingly, the stilbene compounds in the distillation products can be made to react for instance to form esters or salts, in which case their separation is further facilitated. A classic way of separating phenolic compounds, which the pinosylvin compounds, too, often are, from carboxylic acids, is to treat a mixture of them with sodium hydrogen carbonate, in which case the acids form salts but the phenolic compounds do not.

The present invention can be utilized for instance in the production of pinosylvin, piceatannol, rhapontigenin, resveratrol or pterostilbene or any other stilbene derivative which has one or more hydroxyl and/or ether groups, or any other derivative of the said stilbene compounds.

The following non-limiting examples illustrate the present invention:

EXAMPLE 1

Crude fatty acid, which is produced in a tall oil distillery, was evaporated in a short-path evaporator at a pressure of 5 mbar(a) and a temperature of 220 to 240° C. As a result, a distillate flow was obtained which formed 85 to 97% of the feed, and a bottoms product flow which, correspondingly, formed 3 to 15% of the feed.

When the bottoms product was analysed by using the GCMS method, the product was found to comprise 3 to 30 weight-% of esters of pinosylvin monomethyl ether, together with fatty acids or resin acids.

Earlier analyses had failed to discover or demonstrate the existence of these compounds.

EXAMPLE 2

The bottoms product of the test described above was treated for a period of four hours, using a 15 weight-% lye-water mixture (NaOH), while being heated and mixed. After that, the aqueous phase was separated from the organic phase. The organic phase was evaporated anew in a short-path evaporator at a pressure of 5 mbar(a) and a temperature of 160 to 270° C.

In the distillates generated, the percentage of the pinosylvin monomethyl ether varied in the range of 25 to 60 weight-%.

EXAMPLE 3

In an alternative concentration process, the bottoms product in the crude fatty acid evaporation test which was applied in Example 1 was first treated, while being heated and mixed, using a 15-weight-% lye solution, with the purpose of breaking up the esters in the solution into free alcohols and into salts of acids.

After that, 30 weight-% of sulphuric acid was added into the organic phase. The reaction mixture was allowed to settle and the aqueous phase that was generated was separated from the organic phase. The organic phase was directed to the short-path evaporation (5 mbar(a), 160 to 270° C.), in which case the distillate generated was a flow which comprised 25 to 60 weight-% of pinosylvin monomethyl ether.

It should be noted that the volatility of the pinosylvin monomethyl ester differs from the volatilities of fatty acids or resin acids so far that it is possible to use traditional vacuum distillation to purify pinosylvin monomethyl ester even further by way of concentrating it.

The invention claimed is:

1. A composition suitable for manufacturing stilbene compounds, which comprises esters of pinosylvin and that it is enriched in relation to these, wherein the acid part of said esters is derived from linoleic acid, linolenic acid, oleic acid, or a tricyclic, aliphatic or aromatic carboxylic acid.

2. The composition according to claim 1, wherein the ester percentage of the pinosylvin in the composition is at least approximately 3 weight-%, calculated from the total weight of the composition.

3. The composition according to claim 1, wherein said acid part is derived from linoleic acid, linolenic acid or oleic acid.

4. The composition according to claim 1, wherein said acid part of the esters is derived from a tricyclic, aliphatic or aromatic carboxylic acid.

5. The composition according to claim 4, wherein said acid part is derived from abietic acid, dehydroabietic acid, neoabietic acid, palustrene acid, pimaric acid or levopimaric acid.

6. The composition according to claim 1, wherein the concentration of the dry matter or of the pinosylvin of the composition is approximately 3-50 weight-%.

7. The composition according to claim 6, wherein the concentration of the ester of the pinosylvin is approximately 5-95 weight-%.

8. The composition according to claim 1, which comprises a fraction of the distillation or evaporation of crude tall oil, which fraction has been enriched in order to increase the portion of pinosylvin or of the esters of its derivatives.

9. The composition according to claim 1, which comprises tall oil pitch, which has been concentrated in order to increase the portion of pinosylvin or esters of its derivatives.

10. The composition according to claim 1, wherein the portion of esters of pinosylvin, or a mixture of two or more of the compounds, is approximately 1-95 weight-%.

11. A method of producing a composition suitable for manufacturing pinosylvin and its compounds, said method comprises recovering a fraction of the distillation or evaporation of crude tall oil as the overhead product of a column or of an evapopration used in the distillation of tall oil, wherein said fraction contains esters of pinosylvin or its derivatives, which fraction is then enriched in relation to the esters of pinosylvin or its derivatives and wherein stilbene compounds, which form part of the overhead product, are esterified with lower alkane acids or fatty acids or resin acids, or the stilbene compounds are modified by means of chemical technology methods to form compounds that are easier to separate from the rest of the fraction then is the original compound.

12. The method according to claim 11, wherein the feeding flow of the distillation or the evaporation is a fraction, which is the overhead product, the bottoms product or a side draw-off taken from a chosen intersection, of a distillation column or an evaporator of the tall oil distillery.

13. The method according to claim 11 or 12, wherein a fraction, which contains esters of pinosylvin or its derivatives, is recovered as the bottoms fraction of the fatty acid distillation column.

14. The method according to claim 11 or 12, wherein said fraction, which contains esters of pinosylvin or its compounds, is tall oil pitch.

15. The method according to claim 11, wherein any overhead product of the tall oil distillery or other product flow is concentrated in relation to stilbene or its compounds, after the esterification of said compounds.

16. The method according to claim 11, wherein a composition suitable for the manufacturing of stilbene compounds is formed by combining the bottoms fraction of the fatty acid distillation column and the overhead product of the distillation of the light fatty acids.

17. The method according to claim 11, wherein in order to improve the ester yield from the stilbene compounds, the crude tall oil or one of its distillation fractions is brought to such conditions which facilitate the generation of esters, through a reaction between pinosylvin or pinosylvin monomethyl ether and fatty acids or resin acids.

18. The method according to claim 17, wherein crude tall oil or its distillation fraction is contacted with an additive which catalyzes the esterification.

19. The method according to claim 18, wherein oxygen is used as the additive which catalyzes the esterification.

20. The method according to claim 18 or 19, wherein a compound, which discharges hydrogen ions when it reacts with fatty or resin acids, is used as the additive which catalyzes the esterification.

21. A resin acid ester of pinosylvin or of us monomethyl ether wherein the acid part is derived from abietic acid, dehydroabietic acid, neoabietic acid, palustrene acid, pimaric acid or levopimaric acid.

22. The composition according to claim 2, wherein said ester percentage is approximately 3-80 weight-%.

23. The composition according to claim 2, wherein said ester percentage is approximately 5-50 weight-%.

24. The composition according to claim 7, wherein said concentration of the ester is approximately 10-60 weight-%.

25. The composition according to claim 7, wherein said concentration of the ester is approximately 15-50 weight-%.

26. The composition according to claim 10, wherein said portion is approximately 10-60 weight-%.

27. The composition according to claim 10, wherein said portion is approximately 15-50 weight-%.

28. A composition suitable for manufacturing stilbene compounds, which comprises 5 to 95 weight % of esters of pinosylvin, wherein the acid part of said esters is derived from linoleic acid, linolenic acid, oleic acid, or a tricyclic, aliphatic or aromatic carboxylic acid.

29. The composition according to claim 21, wherein said acid part is derived from linoleic acid, linolenic acid or oleic acid.

* * * * *